United States Patent [19]
Krihak et al.

[11] Patent Number: 5,945,286
[45] Date of Patent: Aug. 31, 1999

[54] ELECTROCHEMICAL-BASED MOLECULAR DETECTION APPARATUS AND METHOD

[75] Inventors: Michael Krihak, Phoenix; Chan-Long Shieh, Paradise Valley, both of Ariz.

[73] Assignee: Motorola, Inc., Schaumburg, Ill.

[21] Appl. No.: 08/956,676

[22] Filed: Oct. 23, 1997

[51] Int. Cl.[6] .................................................. C12Q 1/68
[52] U.S. Cl. .................................. 435/6; 422/50; 422/55; 422/56; 422/57; 422/68.1; 422/82.01; 435/283.1; 435/285.2; 435/287.1; 435/287.2; 435/287.7; 435/287.9; 935/77; 935/78
[58] Field of Search .......................... 422/50, 55, 56, 422/57, 68.1, 69, 82.01; 435/6, 283.1, 285.2, 287.1, 287.2, 287.7, 287.9; 530/300, 344; 536/22.1, 23.1, 25.4; 935/77.78

[56] References Cited

U.S. PATENT DOCUMENTS

| 5,599,695 | 2/1997 | Pease et al. | 435/91.1 |
| 5,632,957 | 5/1997 | Heller et al. | 422/68.1 |
| 5,653,939 | 8/1997 | Hollis et al. | 422/50 |
| 5,700,922 | 12/1997 | Cook | 536/23.1 |

*Primary Examiner*—Ardin H. Marschel
*Attorney, Agent, or Firm*—Eugene A. Parsons; William E. Koch

[57] ABSTRACT

A molecular detection apparatus including an electrode, a peptide nucleic acid probe covalently bonded to the electrode and a protective layer covering portions of the electrode not having attached probes which prevents oxidation/reduction of intercalator molecules.

12 Claims, 1 Drawing Sheet

ELECTROCHEMICAL-BASED MOLECULAR DETECTION APPARATUS AND METHOD

FIELD OF THE INVENTION

The present invention relates to electrochemical molecular detection devices.

BACKGROUND OF THE INVENTION

Recently, an increased effort has been directed toward the development of chips for molecular detection. In general, a molecular detection chip includes a substrate on which an array of binding sites is arranged. Each binding site (or hybridization site) has a respective molecular receptor (or probe) which binds or hybridizes with a molecule having a predetermined structure. A sample solution is applied to the molecular detection chip, and molecules in the sample bind or hybridize at one or more of the binding sites. The particular binding sites at which hybridization occurs are detected, and one or more molecular structures within the sample are subsequently deduced.

Of great interest are molecular detection chips for gene sequencing. These chips, often referred to as DNA chips, utilize an array of selective binding sites each having respective single-stranded DNA probes. A sample of single-stranded DNA fragments, referred to as target DNA, is applied to the DNA chip. The DNA fragments attach to one or more of the DNA probes by a hybridization process. By detecting which DNA probes have a DNA fragment hybridized thereto, a sequence of nucleotide bases within the DNA fragment can be determined.

Various approaches have been utilized to detect a hybridization event at a binding site. Many different approaches such as optical and electrical detection have been developed, but only electrical detection will be addressed herein.

The specific approach of interest is electrochemical based detection. In this approach a standard three-electrode potentiostat including an auxiliary electrode, a reference electrode and a working electrode is provided. DNA probes are covalently bonded to the surface of the working electrode by linker groups. Exposure of the single stranded DNA probes to complementary single-stranded DNA in solution will result in a hybridization reaction specifically dictated by the DNA base sequence. By applying voltemetric measurement techniques, DNA hybridization reactions are measured by observing the change in peak current caused by an oxidation/reduction reaction. This reaction is completed by introducing an intercalator that specifically binds to the minor groove of double stranded DNA through electrostatic interactions. As a result, the current peak due to oxidation/ reduction of the intercalator bound to the hybridized DNA will indicate the hybridization event.

The problem with detecting a current peak associated with the oxidation/reduction reaction of the intercalator at the hybridization event is background current. The sensitivity of these types of devices is limited because intercalators may have an oxidation/reduction reaction with the working electrode surface, resulting in background current. Furthermore, while the intercalators have a tendency to bind to the minor groove of a double stranded DNA molecule through electrostatic interactions, they will also bind to a single stranded DNA, although not as readily. This further reduces sensitivity.

It would be highly advantageous, therefore, to remedy the foregoing and other deficiencies inherent in the prior art.

Accordingly, it is an object of the present invention to provide a new and improved method and apparatus for identifying molecules.

Another object of the present invention is to provide a new and improved method and apparatus for identifying molecules employing electrochemical detection.

And another object of the present invention is to provide a new and improved method and apparatus for electrochemical detection of molecules, having reduced background current.

Yet another object of the present invention is to provide a new and improved method and apparatus for electrochemical detection of molecules, having increase sensitivity.

Still another object of the present invention is to provide a new and improved method and apparatus for electrical detection of molecules, employing a probe which limits the attraction of intercalators thereto.

SUMMARY OF THE INVENTION

Briefly, to achieve the desired objects of the instant invention, in accordance with a preferred embodiment thereof, provided is a molecular detection apparatus including an electrode, a peptide nucleic acid probe covalently bonded to the electrode, and a protective layer covering portions of the electrode not having attached probes which prevents oxidation/reduction of intercalator molecules.

In a more specific aspect, an electrical detector is included which is in electrical communication with the electrode to detect a potential/current peak occurring due to oxidation/ reduction of an interaction of intercalator molecules with a hybridized target molecule and peptide nucleic acid probe.

Also provided is a method of identifying a target molecule including the steps of providing an electrode having a peptide nucleic acid probe and a protective layer covering portions of the electrode not having attached probes which prevents oxidation/reduction of intercalator molecules. An electrical detector in electrical communication with the electrode is provided. A solution containing a target molecule and intercalator molecules is supplied and combined with the peptide nucleic acid probe whereby the target molecule is free to hybridize with the peptide nucleic acid probe and the intercalator molecules are free to bond with the hybridized target molecule and peptide nucleic acid probe. A potential/current peak resulting from the oxidation/ reduction of intercalator molecules with the hybridized target molecule and peptide nucleic acid probe is sensed to determine the hybridization event.

BRIEF DESCRIPTION OF THE DRAWINGS

The foregoing and further and more specific objects and advantages of the instant invention will become readily apparent to those skilled in the art from the following detailed description of the preferred embodiment thereof taken in conjunction with the drawings in which.

DETAILED DESCRIPTION OF A PREFERRED EMBODIMENT

The present invention advantageously provides a molecular detection apparatus which detects the binding or hybridization of a target molecule to a molecular receptor by sensing a current peak associated with the oxidation/ reduction reaction of intercalator molecules. The oxidation/ reduction reaction is established when intercalators bind to the minor groove of a double stranded molecule created by the hybridization of a target molecule and a molecular receptor.

Figure 1:
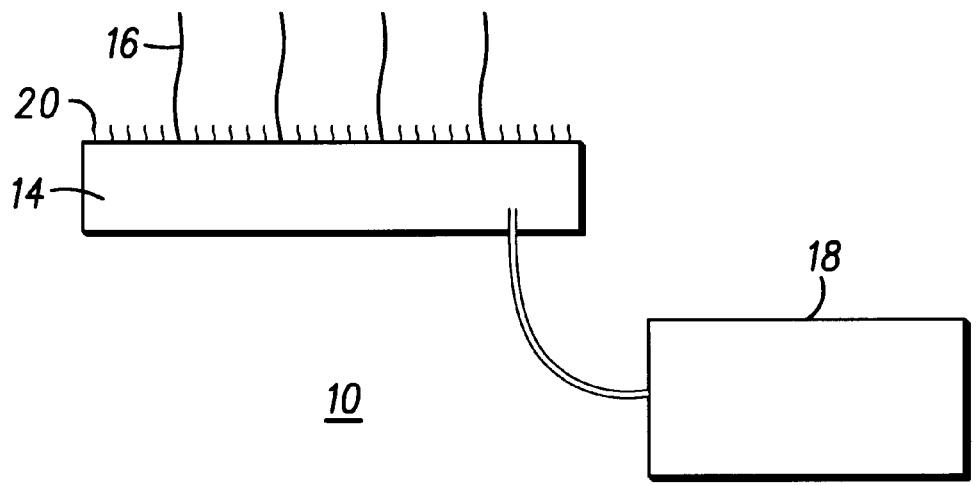
FIG. 1 is a simplified sectional side view of a molecular detection apparatus according to the present invention.

Turning now to the drawings in which like reference characters indicate like elements throughout the several views, attention is first directed to FIG. 1 which illustrates a molecular detection apparatus generally designated 10. Molecular detection apparatus 10 includes an electrode 14 on which is formed a plurality of peptide nucleic acid molecular receptors (probes) 16. In the preferred embodiment, probes 16 are covalently bonded to the surface of electrode 14 by linker groups in a known manner. Each of molecular receptors 16 carried by electrode 14 are substantially identical. It will be understood that a great many probes 16 may be carried by electrode 14 or as few as one probe.

In general, peptide nucleic acid molecular receptors 16 are selected in dependence upon a type of target molecule which is to be detected. Each probe 16 includes a synthetic molecule that has a specific affinity to the target molecule to be detected. The synthetic molecule includes a chain of at least one nucleotide which hybridizes with a complementary chain of at least one nucleotide included in the target molecule. In the present invention, probes 16 include a peptide nucleic acid (PNA) composed of nucleotide bases carried by a peptide backbone for detecting a corresponding, complementary base sequence in the target molecule.

PNA binds to single stranded DNA the same as complimentary DNA, only with more affinity and greater specificity. The use of PNA instead of DNA as probes 16 provides for greater sensitivity because PNA has no inherent charge as does DNA. This will be explained below. It is noted, however, that the scope of the invention is not limited to sensing the hybridization of a DNA molecule to PNA molecular receptors 16. For example, embodiments of the present invention can also be utilized to detect RNA hybridization.

Molecular detection apparatus 10 further includes an electrical detector 18, in electrical communication with electrode 14 to detect a potential/current peak occurring due to oxidation/reduction of an interaction of intercalator molecules with a hybridized target molecule and peptide nucleic acid probe 16. Electrical detector 18 is not described in detail, as any conventional electrical detection device typically used in voltammetric measurement techniques can be employed. As a specific example, electrical detector 18 can be a standard three-electrode potentiostat having an auxiliary electrode, a reference electrode and a working electrode (electrode 14).

A protective layer 20 covers portions of electrode 14 not having attached probes 16. This prevents oxidation/reduction of intercalator molecules to the surface of electrode 14. In the preferred embodiment, protective layer 20 is a monolayer of a thiol base molecule which is inert and can be self-assembled on the surface of electrode 14.

Figure 2:
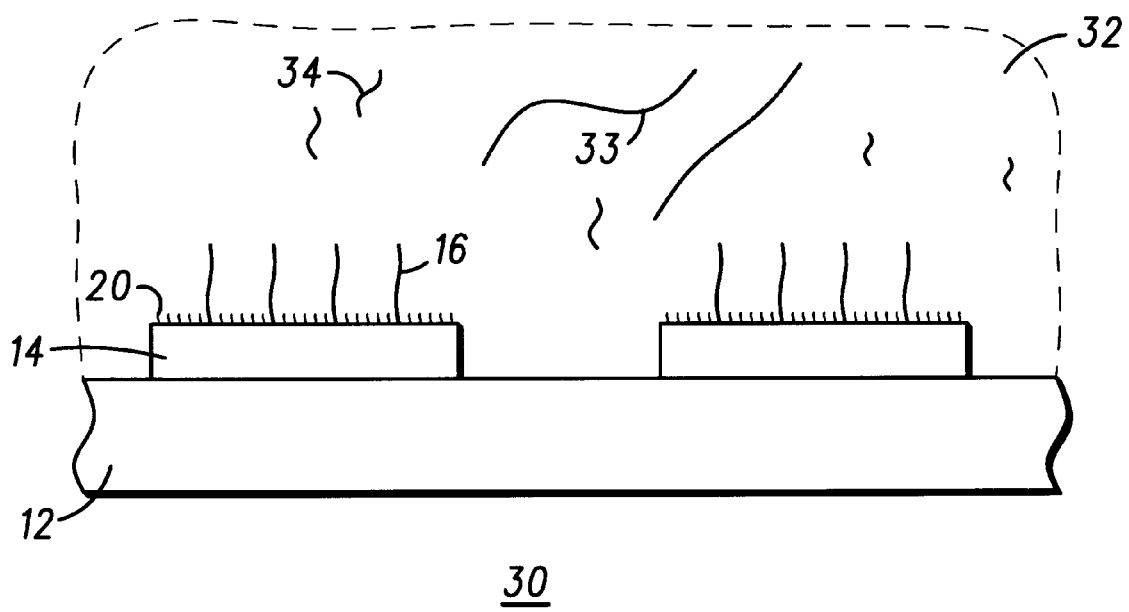
FIG. 2 a simplified sectional side view of an array of the molecular detection apparatus of FIG. 1.

Turning now to FIG. 2, a side view of a molecular detection apparatus 30 including an array of electrodes 14 carried by a substrate 12 is illustrated. Peptide nucleic acid probes 16 on respective electrodes 14 differ in base sequence for simultaneous detection of a plurality of different target molecules within a single array.

To identify a molecule, a solution 32 containing target molecules 33 and intercalator molecules 34 is brought into contact with probes 16. Target molecules 33 are free to hybridize with peptide nucleic acid probes 16. It will be understood that substantially any number of target molecules 33 may be present in the solution. Intercalator molecules 34 are free to bond with the double stranded molecule created by the hybridization of target molecules 33 and peptide nucleic acid probes 16.

Hybridization reactions are measured by observing the change in peak current caused by an oxidation/reduction reaction. This reaction is completed by introducing intercalator molecules 34 which specifically bind to the minor groove of a double stranded molecule through electrostatic interactions. As a result, the current peak due to oxidation/reduction of the intercalator bound to the hybridized molecule will indicate the hybridization event.

A potential/current peak resulting from the oxidation/reduction of intercalator molecules with the hybridized target molecule and peptide nucleic acid probe is sensed. Determining a current peak is accomplished by using a reference potential/current to determine the potential/current peak resulting from the oxidation/reduction of intercalator molecules with the hybridized target molecule and peptide nucleic acid probe. Sensitivity is increased by widening the difference between the reference potential/current and the potential/current peak.

In conventional devices, the background current caused by intercalators having an oxidation/reduction reaction with the working electrode surface and binding to single stranded DNA probes having an inherent charge which can attract intercalator molecules, narrows the difference, reducing sensitivity and requiring a relatively large potential/current peak to be noticeable over the background. By forming protective layer 20 on electrodes 14 and by using probes 16 formed of single stranded peptide nucleic acid molecules, background current is substantially reduced, increasing sensitivity. The reduction in background current occurs because protective layer 20 and probes 16 do not have any inherent charge which can attract intercalator molecules 34. Since intercalator molecules 34 are not attracted they will not contribute to an oxidation/reduction reaction to produce a current.

Thus provides is a new and improved method and apparatus for identifying molecules employing electrochemical detection having sensitivity by employing molecular receptors having no inherent charge.

Various modifications and changes to the embodiments herein chosen for purposes of illustration will readily occur to those skilled in the art. Other modifications and variations may be made by those skilled in the art without departing from the scope of the invention as defined by the following claims.

Having fully described and disclosed the present invention and preferred embodiment thereof in such clear and concise terms as to enable those skilled in the art to understand and practice same, the invention claimed is:

1. A molecular detection apparatus comprising:
   an electrode;
   a peptide nucleic acid probe covalently bonded to the electrode, the peptide nucleic acid probe including a chain of at least one nucleotide;
   a protective layer including a thiol base molecule covering portions of the electrode not having attached probes which prevents oxidation/reduction of intercalator molecules; and
   an electrical detector in electrical communication with the electrode to detect a potential/current peak occurring due to oxidation/reduction of an interaction of intercalator molecules with a hybridized target molecule and peptide nucleic acid probe, wherein the target molecule includes one of a DNA molecule and an RNA molecule in a complementary chain of at least one nucleotide.

2. An apparatus as claimed in claim 1 wherein the electrical detector includes a reference electrode.

3. An apparatus as claimed in claim 1 including in addition the electrode having a plurality of identical peptide nucleic acid probes covalently bonded thereto.

4. An apparatus as claimed in claim 3 including in addition a plurality of electrodes mounted in spaced apart relation on a support, each electrode having a plurality of identical peptide nucleic acid probes covalently bonded thereto, the peptide nucleic acid probes having a different sequence in respective electrodes.

5. A molecular detection apparatus comprising:
   an electrode;
   a peptide nucleic acid probe covalently bonded to the electrode and positioned in a solution containing target molecules and intercalator molecules, the peptide nucleic acid probe including a chain of at least one nucleotide;
   a protective layer including a thiol base molecule covering portions of the electrode not having attached probes which prevents oxidation/reduction of intercalator molecules; and
   an electrical detector in electrical communication with the electrode to detect a potential/current peak occurring due to oxidation/reduction of an interaction of intercalator molecules with a hybridized target molecule and peptide nucleic acid probe, wherein the target molecule includes one of a DNA molecule and an RNA molecule in a complementary chain of at least one nucleotide.

6. An apparatus as claimed in claim 5 wherein the electrical detector includes a reference electrode.

7. An apparatus as claimed in claim 5 including in addition the electrode having a plurality of identical peptide nucleic acid probes covalently bonded thereto.

8. An apparatus as claimed in claim 7 including in addition a plurality of electrodes mounted in spaced apart relation on a support, each electrode having a plurality of identical peptide nucleic acid probes covalently bonded thereto, the peptide nucleic acid probes having a different sequence in respective electrodes.

9. A method of identifying a target molecule comprising the steps of:

providing an electrode having a peptide nucleic acid probe, including providing a chain of at least one nucleotide attached to a peptide backbone, and a protective layer including a thiol base molecule covering portions of the electrode not having attached probes which prevents oxidation/reduction of intercalator molecules;

providing an electrical detector in electrical communication with the electrode;

supplying a solution containing a target molecule including one of a DNA molecule and an RNA molecule and intercalator molecules;

combining the peptide nucleic acid probe and the solution;

whereby the target molecule is free to hybridize with the peptide nucleic acid probe and the intercalator molecules are free to bond with the hybridized target molecule and peptide nucleic acid probe; and sensing a potential/current peak resulting from the oxidation/reduction of intercalator molecules with the hybridized target molecule and peptide nucleic acid probe.

10. A method as claims in claim 9 wherein the step of sensing includes using a reference potential/current to determine the potential/current peak resulting from the oxidation/reduction of intercalator molecules with the hybridized target molecule and peptide nucleic acid probe.

11. A method as claimed in claim 9 wherein the step of providing the electrode includes providing the electrode having a plurality of identical peptide nucleic acid probes covalently bonded thereto.

12. A method as claimed in claim 11 wherein the step of providing the electrode includes providing a plurality of electrodes mounted in spaced apart relation on a support, each electrode having a plurality of identical peptide nucleic acid probes covalently bonded thereto, the peptide nucleic acid probes having a different sequence in respective electrodes.

\* \* \* \* \*